(12) United States Patent
Andre et al.

(10) Patent No.: US 7,935,359 B2
(45) Date of Patent: May 3, 2011

(54) USE OF L 2-THIOHISTIDINE OR ONE OF ITS DERIVATIVES AS A DEPIGMENTING AGENT IN COSMETICS

(75) Inventors: Patrice Andre, Neuville aux Bois (FR); Clarisse Marteau, Dry (FR); Isabelle Renimel, Trainou (FR); Marielle Moreau, Marcq (FR)

(73) Assignee: LVMH Recherche, Jean de Brave (FR)

( * ) Notice: Subject to any disclaimer, the term of this patent is extended or adjusted under 35 U.S.C. 154(b) by 676 days.

(21) Appl. No.: 12/005,823

(22) Filed: Dec. 28, 2007

(65) Prior Publication Data

US 2008/0161377 A1    Jul. 3, 2008

(30) Foreign Application Priority Data

Dec. 29, 2006  (FR) ..................... 06 56063

(51) Int. Cl.
*A61F 2/00*     (2006.01)
*A61K 31/4172*  (2006.01)
*A61Q 19/00*    (2006.01)

(52) U.S. Cl. ....................... 424/401; 514/400

(58) Field of Classification Search .................. 424/401
See application file for complete search history.

(56) References Cited

U.S. PATENT DOCUMENTS

| 5,438,151 A * | 8/1995 | Yadan et al. ............... 548/324.1 |
| 6,056,965 A | 5/2000 | Yadan et al. |
| 2003/0095959 A1 * | 5/2003 | Mayne ........................ 424/94.4 |

FOREIGN PATENT DOCUMENTS

| EP | 0 483 426 A1 | 5/1992 |
| FR | 2 867 384 | 9/2005 |
| JP | 1973-044442 | 6/1973 |
| JP | 56-147704 | 11/1981 |
| WO | WO 95/34280 | 12/1995 |
| WO | WO 2006/124992 A1 | 11/2006 |

* cited by examiner

*Primary Examiner* — Richard Schnizer
*Assistant Examiner* — Audrea J Buckley
(74) *Attorney, Agent, or Firm* — Merchant & Gould PC

(57) ABSTRACT

The invention relates to the use of L-2-thiohistidine, or a cosmetically acceptable salt or ester of its acid group, as a depigmenting agent in a cosmetic composition or for the preparation of a cosmetic composition. It further relates to a method of cosmetic care for toning down or eliminating pigment spots on the skin and/or lightening the complexion by the application of this cosmetic composition. The invention provides a highly depigmenting composition.

Figure 1:
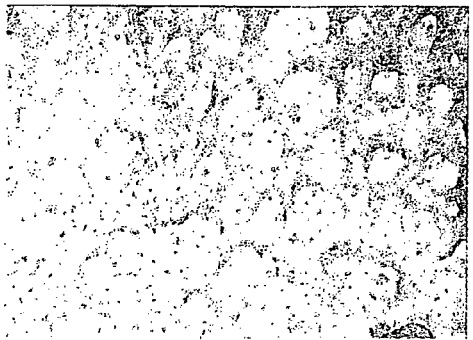

12 Claims, 1 Drawing Sheet ium, ammonium, $(HOCH_2CH_2)_3NH^+$ or $(C_2H_5)_3NH^+$ salts
USE OF L 2-THIOHISTIDINE OR ONE OF ITS DERIVATIVES AS A DEPIGMENTING AGENT IN COSMETICS The present invention relates essentially to the use of L-2-thiohistidine or one of its derivatives as a depigmenting agent in a cosmetic composition or for the manufacture of a cosmetic composition, and to a method of cosmetic care for toning down or eliminating pigment spots on the skin and/or lightening the complexion.

STATE OF THE ART

Numerous depigmenting agents are known in the state of the art.

In particular, the document JP 1973-044442 discloses a cosmetic composition with a depigmenting effect which contains ergothioneine.

Although they are active, the depigmenting agents of the prior art have various disadvantages. In fact, they often have a complex formulation and/or a degree of toxicity, and/or they can also exhibit unwanted side effects, particularly if they are irritant or allergizing.

L-2-thiohistidine, also known as L-2-mercaptohistidine, corresponds chemically to alpha-amino-2,3-dihydro-2-thioxo-1H-imidazole-4-propanoic acid and has the CAS registration number 2002-22-4.

This product has already been used in the field of cosmetics for its deodorizing effect.

The Japanese document JP 56-147 704 discloses the use of compounds based on tropolone in the form of salts with basic amino acids, including thiohistidine. The depigmenting activity is attributed to the tropolone-based compounds, the salt form making it possible to improve the solubilization of the tropolone compounds in water and to increase the depigmenting effect.

It must further be observed that none of the Examples in said document relates to thiohistidine.

Under these conditions it is clear that thiohistidine was not tested and therefore that it was not obvious to those skilled in the art to discover its depigmenting activity.

Tropolone-based compounds in the form of salts with thiohistidine are excluded from the present invention.

OBJECTS OF THE INVENTION

The main object of the present invention is to provide a novel depigmenting agent which has a very good depigmenting efficacy without substantial side effects and without substantial toxicity at the doses used. One object of the present invention is to provide such a novel depigmenting agent in a simple manner that allows it to be used on the industrial and cosmetic scale.

SUMMARY OF THE INVENTION

According to a first aspect, the present invention relates to the use of L-2-thiohistidine, or a cosmetically acceptable salt or ester of its acid group, as a depigmenting agent in a cosmetic composition or for the preparation of a cosmetic composition.

In particular, such a composition can be used to depigment human skin.

According to a second aspect, the present invention further relates to a method of cosmetic care selected from toning down or eliminating pigment spots on the skin and lightening the skin complexion, comprising delivering to skin areas in need thereof, a depigmenting effective amount of at least one depigmenting agent comprising a thiohistidine component selected from L-2-thiohistidine, a L-2-thiohistidine salt and a L-2-thiohistidine ester.

In one particular embodiment of the invention, the salts of thiohistidine with a tropolone-based compound are excluded, particularly tropolone-based compounds such as those described in the Japanese document JP 56-147 704. Cited tropolone-based compounds such as the salts of thiohistidine with tropolone, stipitatic acid, puberulic acid, stipitic acid, puberulonic acid, alpha-thujaplicin, beta-thujaplicin, gamma-thujaplicin, nootkatin, purpurogallin and colchiceine are more particularly excluded.

Within the framework of each of these features, L-2-thiohistidine will preferably be used as the depigmenting agent.

In one variant, it is also possible to use a monovalent or divalent salt of the L-2-thiohistidine acid group.

The sodium, potassium, lithium, barium, magnesium, calcium, ammonium, $(HOCH_2CH_2)_3NH^+$ or $(C_2H_5)_3NH^+$ salts may be mentioned as preferred salts of the acid group.

The linear or branched $C_1$ to $C_4$ alkyl or hydroxyalkyl esters of L-2-thiohistidine may be mentioned as preferred esters of the acid group.

Within the framework of each of these aspects, 'effective amount' is understood as meaning the minimum amount necessary to obtain a significant depigmenting activity.

In general, the recommended concentration of L-2-thiohistidine or its salt or ester will vary within wide limits of between 0.0001 and 1% by weight of the final composition.

A preferred range will be between 0.001% and 0.1% by weight.

L-2-thiohistidine or its salt or ester may also be used in combination with at least one other depigmenting agent.

Within the framework of the invention, at least one other cosmetically active agent, such as an antioxidant or a soothing agent, may also be used in the composition.

'Antioxidant' is understood as meaning an active substance that is capable of trapping free radicals and/or reactive oxygen substances.

Such an antioxidant may be selected especially from polyphenols, selenium derivatives such as ebselen, vitamin E derivatives and idebenone.

'Soothing agent' is understood as meaning an active substance with a skin soothing effect which makes it possible to prevent and/or combat non-pathological skin manifestations of inflammatory origin, particularly those associated with the release of cytokines, especially interleukin-8, and/or prostaglandins.

Such a soothing agent may be selected especially from soothing agent is selected from the group consisting of an extract of *Scutellaria baicalensis*, an extract of *Prunella vulgaris* an extract of green tea, a glycyrrhetinic component, glycyrrhetinic acid, ammonium glycyrrhetinate, potassium glycyrrhetinate, stearyl glycyrrhetinate, and any mixture thereof.

Furthermore, as can also be easily understood by those skilled in the art, any excipient may be added in order to manufacture said cosmetic composition, particularly, of course, excipients or agents that are cosmetically acceptable.

It is also possible, of course, to add exfoliants as well as a variety of preservatives, perfumes, etc.

Furthermore, the cosmetic composition of the invention can take different forms, particularly lotions, gels, emulsions, creams, powders, make-up foundations or sticks.

Those skilled in the art will easily be able to prepare the composition of the invention by any means conventionally used to prepare this type of composition.

Furthermore, those skilled in the art are perfectly capable of selecting the areas of skin that are in need of depigmentation. These are generally the areas of corporeal skin that are most exposed to solar radiation or most sensitive to the external environment, such as the face and upper and lower limbs. In the case of liver spots or spots associated with localized hyperpigmentations due to melanocytic hyperactivity, such as actinic lentigo, these can of course be found in any area of the body.

Other objects, characteristics and advantages of the invention will become clearly apparent from the following explanatory description referring to several currently preferred embodiments of the invention, which are given simply by way of illustration and cannot therefore limit the scope of the invention in any way.

Example 1 below is given with reference to FIGS. 1 to 5, which respectively show negatives obtained by optical microscopy on epidermis treated with:
FIG. 1: L-DOPA,
FIG. 2: kojic acid,
FIG. 3: ergothioneine,
FIG. 4: L-2-thiohistidine at 50 µg/ml,
FIG. 5: L-2-thiohistidine at 150 µg/ml.

In the Examples, the percentages are given by weight, the temperature is room temperature and the pressure is atmospheric pressure, unless indicated otherwise.

The Examples form an integral part of the invention, and any technical characteristic that appears novel relative to any prior art is claimed as such and as a general means.

EXAMPLE 1 ACCORDING TO THE INVENTION

Comparative Tests Demonstrating the Depigmenting Activity of L-2-Thiohistidine

In this Example a quantitative comparative test is carried out on a separated epidermis in order to show the depigmenting activity of L-2-thiohistidine compared with various depigmenting agents known in the prior art, especially kojic acid or ergothioneine, and also compared with a control sample comprising DOPA oxidase.

The procedure of this test is similar to that described in Example II of the LVMH RECHERCHE document FR-A-2, 867,384 published on 16 Sep. 2005, to which those skilled in the art may usefully refer and which is incorporated by reference.

Procedure

Frozen mammary epidermis originating from plastic surgery on a 39-year-old woman, reference P148AB39, are separated by incubation in 2N NaBr for 1 h 45 min at 37° C. They were fixed in a formalized fixative, buffered, rinsed and brought into contact with a volume/volume mixture of L-DOPA/active principle solution. After incubation, they were rinsed and mounted between slides and cover slips with mounting medium.

The epidermis were observed by optical microscopy with a magnification of 10.

Figure 2:
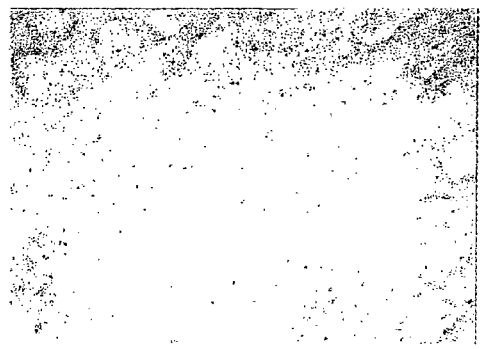
Figure 3:
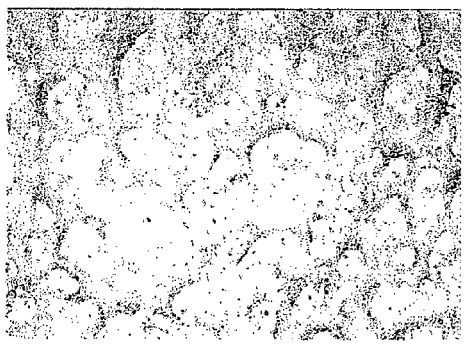
Figure 4:
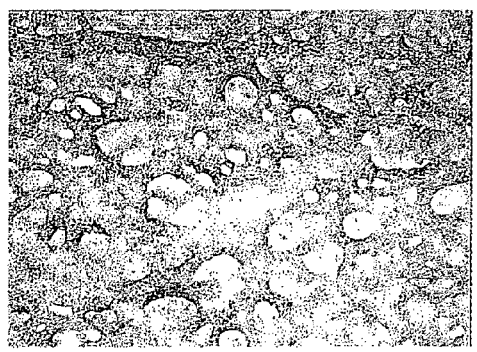
Figure 5:
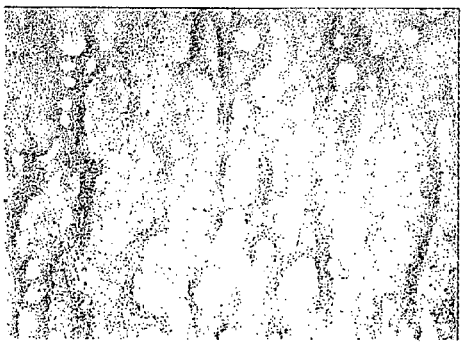

The following results are observed:
a) with the DOPA control, cf. FIG. 1 attached, the melanocytes are distinctly visible and well pigmented;
b) with kojic acid at a concentration of 150 µg/ml as comparative depigmenting agent, cf. FIG. 2, it is seen that the melanocytes are only slightly visible and that there is therefore a very good depigmenting activity, which is close to 75% in this case;
c) with ergothioneine at a concentration of 50 µg/ml as comparative depigmenting agent, cf. FIG. 3, it is seen that the melanocytes are fairly visible and still fairly well pigmented, a slight depigmenting activity close to 45% being observed;
d) with L-2-thiohistidine at a concentration of 50 µg/ml, according to the invention, cf. FIG. 4, it is seen that the melanocytes are less visible than with ergothioneine at the same concentration, cf. FIG. 3, the depigmenting activity, in this case 60%, therefore being good;
e) with L-2-thiohistidine used as depigmenting agent at a concentration of 150 µg/ml, cf. FIG. 5, it is seen that the melanocytes are now very poorly visible because they are very poorly pigmented, the depigmenting activity being 75% in this case, i.e. a very good depigmenting activity.

The depigmenting activity which can be seen in FIGS. 1 to 5 was quantified statistically by counting the grains of melanin over a series of 3 tests. The values are shown in the Table below, in which the values obtained for the Student test are specified for ergothioneine versus L-2-thiohistidine and for kojic acid versus L-2-thiohistidine at the same concentration. The Student test is said to be significant if the value obtained is less than 0.05.

Conclusions

Under the experimental conditions, it is seen that, at a concentration of 150 µg/ml, L-2-thiohistidine has a very good depigmenting activity similar to that of the previously known kojic acid often used as an experimental reference in terms of activity, although its side effects are also well known.

It is also seen that the use of L-2-thiohistidine according to the invention affords a better depigmenting activity than ergothioneine and a similar activity to that of kojic acid at comparable concentration, demonstrating the industrial and cosmetic value of using L-2-thiohistidine as a depigmenting agent in a cosmetic composition.

Various Examples of cosmetic compositions using L-2-thiohistidine as a depigmenting agent will now be described below. In these Examples, all the values are given as percentages by weight, based on the total weight of the composition, unless indicated otherwise.

EXAMPLE 2 ACCORDING TO THE INVENTION

| Cosmetic composition according to the invention in the form of a depigmenting gel | |
|---|---|
| 1°. Depigmenting agent | |
| L-2-thiohistidine | 0.5 |
| 2°. Excipients | |
| Glycol | 3 |
| Polyacrylamide/C13-14 isoparaffin/laureth-7 (Sepigel 305) | 3 |
| Hydrogenated castor oil (Cremophor CO 60) | 2 |
| Polyethylene glycol (Pluriol E 1505) | 1.5 |
| Preservative | 0.5 |
| Perfume concentrate | 0.3 |
| Water | 89.2 |

The procedure for manufacturing the above cosmetic composition is entirely conventional. First of all, the different components of the excipients are mixed in the absence of the gelling agent, which here consists of the Sepigel 305, and then the depigmenting agent is added and finally the gelling agent.

The composition obtained takes the form of a gel with depigmenting activity. This gel can be applied twice a day for two weeks to the areas of skin to be depigmented, affording an effective depigmentation of the areas of skin in question.

EXAMPLE 3 ACCORDING TO THE INVENTION

| Cosmetic composition according to the invention in the form of a depigmenting emulsion | |
|---|---|
| 1°. Depigmenting agent | |
| L-2-thiohistidine | 0.01 |
| 2°. Excipients | |
| Steareth-21 (Brij 721) | 2.5 |
| Glyceryl stearate (Tegin 90) | 1.1 |
| Stearyl alcohol | 5 |
| Glycerol tricaprate/caprylate | 20 |
| Butylene glycol | 3 |
| Glycerol | 2 |
| Preservative | 0.5 |
| Perfume concentrate | 0.5 |
| Water | qsp 100 |

The procedure for manufacturing this cosmetic composition is similar to that of Example 2, the only difference in this case being that, first of all, all the constituents are mixed hot except for the water and the L-2-thiohistidine, which are subsequently added cold.

The L-2-thiohistidine is preferably added to the aqueous phase. A stable emulsion is formed by vigorous mixing, with agitation. This emulsion is then conditioned to give the cosmetic composition in the form of a depigmenting emulsion.

This emulsion can be applied in a similar manner to the depigmenting gel of Example 2 to give the desired depigmenting effect.

EXAMPLE 4 ACCORDING TO THE INVENTION

| Cosmetic composition according to the invention in the form of a depigmenting lotion | |
|---|---|
| 1°. Depigmenting agent | |
| L-2-thiohistidine | 0.001 |
| 2°. Excipients | |
| Butylene glycol | 3 |
| EDTA | 0.1 |
| Solubilizer | 1 |
| Perfume concentrate | 0.3 |
| Alcohol | 5 |
| Water | qsp |

The procedure for manufacturing this composition in the form of a depigmenting lotion is particularly simple. First of all, all the excipients are mixed and then the depigmenting agent, consisting of the L-2-thiohistidine, is added, with agitation, to give a stable solution in the form of a depigmenting lotion.

EXAMPLE 5 ACCORDING TO THE INVENTION

| Cosmetic composition according to the invention in the form of a powder for lightening the complexion | |
|---|---|
| 1°. Depigmenting agent | |
| L-2-thiohistidine | 0.005 |
| 2°. Excipients | |
| Talc | 20 |
| Mica | 20 |
| Sericite | 20 |
| Pigments | 8 |
| Organic powder (Nylon) | 20 |
| Silica | 91.005 |
| Mineral oil or silicone | 3 |

The procedure for manufacturing this cosmetic composition in the form of a powder for lightening the complexion is particularly simple. All the excipients and the depigmenting agent are mixed, with agitation, to give a uniform powder constituting the desired cosmetic composition.

This cosmetic composition in the form of a powder for lightening the complexion can be applied every morning or in the evening, according to personal preference.

EXAMPLE 6 ACCORDING TO THE INVENTION

| Cosmetic composition according to the invention in the form of a lightening make-up foundation | |
|---|---|
| 1°. Depigmenting agent | |
| L-2-thiohistidine | 0.0001 |
| 2°. Excipients | |
| Polyglyceryl-4 isostearate/cetyldimethicone/hexyl laurate | 5.1 |
| Cyclopentasiloxane/cyclohexasiloxane | 5.0 |
| Cetyldimethicone | 1.0 |
| Caprylic/capric triglycerides | 2.2 |
| Octyl stearate | 1.4 |
| Mineral oil | 6.5 |
| Hydrogenated castor oil | 1.2 |
| Beeswax | 0.8 |
| Polymethyl methacrylate | 1.1 |
| $Fe_2O_3$ | 0.45 |
| $TiO_2$ | 5.2 |
| NaCl | 0.6 |
| Perfume concentrate | 0.1 |
| Water | qsp |

This procedure is as in Example 3; all the components are mixed in several steps, as can easily be understood by those skilled in the art, and the L-2-thiohistidine is added cold in the final phase. The mixture is agitated vigorously to give a uniform mixture forming the cosmetic composition in the form of a lightening make-up foundation.

This lightening make-up foundation can be applied daily, at least once a day, to the areas of skin to be depigmented, until the pigmented areas have been lightened.

It is thus seen that the present invention makes it possible very effectively and simply to achieve a depigmenting or lightening effect on pigmented areas of skin. The invention also enables any possible forms of cosmetic composition to be prepared.

TABLE

| | Test 1 | Test 2 | Test 3 | Mean | Standard deviation | Student/control | Student/ ergothioneine | Student/kojic acid |
|---|---|---|---|---|---|---|---|---|
| Control | 409 | 430 | 433 | 424 | 13.08 | | | |
| Kojic acid 150 µg | 124 | 137 | 138 | 133 | 7.81 | 4.97363E−06 | | |
| Ergothioneine 50 µg | 194 | 210 | 190 | 198 | 10.58 | 2.02171E−05 | | |
| Thiohistidine 50 µg | 162 | 178 | 176 | 172 | 8.72 | 9.99899E−06 | 0.000331269 | |
| Thiohistidine 150 µg | 102 | 115 | 116 | 111 | 7.81 | 3.71899E−06 | | 0.026057433 |

What is claimed is:

1. A method of cosmetic care selected from toning down or eliminating pigment spots on the skin and lightening the skin complexion, comprising delivering to skin areas in need thereof, a depigmenting effective amount of at least one thiohistidine selected from L-2-thiohistidine, a L-2-thiohistidine salt and a L-2-thiohistidine ester.

2. The method of claim 1, for depigmenting human skin.

3. The method of claim 1, wherein said thiohistidine is L-2-thiohistidine.

4. The method of claim 1, wherein said thiohistidine is a salt of L-2-thiohistidine selected from a L-2-thiohistidine sodium salt, a L-2-thiohistidine potassium, a L-2-thiohistidine lithium, a L-2-thiohistidine barium, a L-2-thiohistidine magnesium, a L-2-thiohistidine calcium, a L-2-thiohistidine ammonium, a L-2-thiohistidine $(HOCH_2CH_2)_3NH^+$, and a L-2-thiohistidine $(C_2H_5)_3NH^+$ salt.

5. The method of claim 1, wherein said thiohistidine is a linear or branched $C_1$ to $C_4$ alkyl or hydroxyalkyl ester of L-2-thiohistidine.

6. The method of claim 1, wherein said thiohistidine is contained in a cosmetic composition comprising between 0.0001% and 1% by weight of L-2-thiohistidine component.

7. The method of claim 6, wherein said cosmetic composition contains between 0.001% and 0.1% by weight of L-2-thiohistidine.

8. The method of claim 6, wherein said cosmetic composition contains at least one other depigmenting agent.

9. The method of claim 6, wherein said cosmetic composition contains at least one further cosmetically active agent.

10. The method of claim 6, wherein said further cosmetically active agent is selected from an antioxidants and from a soothing agents.

11. The method of claim 10, wherein said cosmetically active agent is an antioxidant selected from antioxidants consisting of a polyphenol, a selenium compound, ebselen, a vitamin E component, vitamin E, idebenone, and any mixture thereof.

12. The method of claim 10, wherein said cosmetically active agent is a soothing agent selected from soothing agents consisting of an extract of *Scutellaria baicalensis*, an extract of *Prunella vulgaris* an extract of green tea, a glycyrrhetinic component, glycyrrhetinic acid, ammonium glycyrrhetinate, potassium glycyrrhetinate, stearyl glycyrrhetinate, and any mixture thereof.

* * * * *